(12) United States Patent
Barak et al.

(10) Patent No.: US 10,073,045 B2
(45) Date of Patent: Sep. 11, 2018

(54) OPTICAL METHOD AND SYSTEM FOR MEASURING ISOLATED FEATURES OF A STRUCTURE

(71) Applicant: NOVA MEASURING INSTRUMENTS LTD., Rehovot (IL)

(72) Inventors: Gilad Barak, Rehovot (IL); Yanir Hainick, Tel-Aviv (IL); Dror Shafir, Kiryat Ono (IL)

(73) Assignee: NOVA MEASURING INSTRUMENTS LTD., Rehovot (IL)

( * ) Notice: Subject to any disclaimer, the term of this patent is extended or adjusted under 35 U.S.C. 154(b) by 656 days.

(21) Appl. No.: 14/416,723

(22) PCT Filed: Jul. 24, 2013

(86) PCT No.: PCT/IL2013/050635
§ 371 (c)(1),
(2) Date: Jan. 23, 2015

(87) PCT Pub. No.: WO2014/016839
PCT Pub. Date: Jan. 30, 2014

(65) Prior Publication Data
US 2015/0212012 A1    Jul. 30, 2015

Related U.S. Application Data

(60) Provisional application No. 61/674,875, filed on Jul. 24, 2012.

(51) Int. Cl.
*G01N 21/894* (2006.01)
*G01N 21/95* (2006.01)
(Continued)

(52) U.S. Cl.
CPC ..... *G01N 21/9501* (2013.01); *G01N 21/8806* (2013.01); *G02B 21/002* (2013.01);
(Continued)

(58) Field of Classification Search
CPC .............. G02B 21/0016; G02B 21/002; G02B 21/0092; G02B 27/46; G01N 21/8806;
(Continued)

(56) References Cited

U.S. PATENT DOCUMENTS 5,208,648 A   5/1993  Batchelder et al.
5,623,339 A * 4/1997  Wickramasinghe ... B82Y 20/00
                                                   356/501
(Continued)

FOREIGN PATENT DOCUMENTS

WO   2004063698 A2   7/2004
WO   2012098550 A1   7/2012
WO   2013011508 A2   1/2013

OTHER PUBLICATIONS

Bucher, Dirk, "A practical guide for fluorescent confocal microscopy", 2018, The Marder Lab, website http://blogs.brandeis.edu/marderlab/a-practical-guide-for-fluorescent-confocal-microscopy/, accessed Apr. 19, 2018.*

(Continued)

*Primary Examiner* — Mischita Henson
(74) *Attorney, Agent, or Firm* — Browdy and Neimark, PLLC (57) ABSTRACT

An optical method and system are presented for use in measurement of isolated features of a structure. According to this technique, Back Focal Plane Microscopy (BFM) measurements are applied to a structure and measured data indicative thereof is obtained, wherein the BFM measurements utilize dark-field detection mode while applying pinhole masking to incident light propagating through an illumination channel towards the structure, the measured data being thereby indicative of a scattering matrix characterizing scattering properties of the structure, enabling identification of one or more isolated features of the structure.

29 Claims, 2 Drawing Sheets

(51) Int. Cl.
*G02B 21/00* (2006.01)
*G02B 27/46* (2006.01)
*G01N 21/88* (2006.01)

(52) U.S. Cl.
CPC ..... *G02B 21/0016* (2013.01); *G02B 21/0092* (2013.01); *G02B 27/46* (2013.01); *G01N 2021/8848* (2013.01); *G01N 2201/061* (2013.01); *G01N 2201/0683* (2013.01); *G01N 2201/12* (2013.01)

(58) Field of Classification Search
CPC ....... G01N 21/9501; G01N 2021/8848; G01N 2201/061; G01N 2201/0683; G01N 2201/12
See application file for complete search history.

(56) References Cited

U.S. PATENT DOCUMENTS

| | | | |
|---|---|---|---|
| 5,838,433 A * | 11/1998 | Hagiwara | G01N 21/95623 356/339 |
| 6,590,645 B1 * | 7/2003 | Chen | G01N 21/8851 257/E21.528 |
| 6,690,469 B1 | 2/2004 | Shibata et al. | |
| 6,813,034 B2 | 11/2004 | Rosenwaig et al. | |
| 7,295,303 B1 | 11/2007 | Vaez-Iravani et al. | |
| 2005/0055609 A1 | 3/2005 | Yuan et al. | |

OTHER PUBLICATIONS

PCT/IL2013/050635 "International Search Report" dated Nov. 10, 2013.

* cited by examiner

Fig. 1

(GENERAL ART)

OPTICAL METHOD AND SYSTEM FOR MEASURING ISOLATED FEATURES OF A STRUCTURE

TECHNOLOGICAL FIELD

This invention is generally in the field of optical measuring/inspecting techniques, and relates to a measurement method and system for characterizing isolated features of a structure, such as a semiconductor wafer.

BACKGROUND

As semiconductor technology progresses, shrinking device dimensions has become an increasingly complex task. Complementing metrology tools, allowing similar improvements in measurement capabilities, are critical for the continual process of this development. Commonly, optical metrology is applied to test structures comprised of a repeating array of identical elements. Optical metrology can acquire highly accurate and precise information on the geometry and material properties characterizing these structures.

In many cases, the test structure configuration (array) is an exact replica of an integrated device, and the device characteristics can be directly inferred from the metrology information obtained on the test structure. When the device itself is comprised of repeating structures, e.g. as common for memory applications, metrology can be applied directly to the device region itself. However, it is often the case that the device is not comprised of an array structure (e.g. in logic applications). In these cases, optical metrology is applied to a periodic structure which is supposed to represent the actual device.

U.S. Pat. No. 6,813,034 describes a technique of analyzing isolated and aperiodic structures with simultaneous multiple angle of incidence measurements. This patent discloses a method for evaluating isolated and aperiodic structure on a semiconductor sample, using focusing of a probe beam from a coherent laser source onto the structure in a manner to create a spread of angles incidence. The reflected light is monitored with an array detector. The intensity or polarization state of the reflected beam as a function of radial position within the beam is measured. Each measurement includes both specularly reflected light as well as light that has been scattered from the aperiodic structure into that detection position. The resulting output is evaluated using an aperiodic analysis to determine the geometry of the structure.

GENERAL DESCRIPTION

There is a need in the art for a novel approach for inspecting structures, such as semiconductor wafers (e.g. progressing on a production line), enabling to characterize an isolated feature, to provide an accurate representation of the actual integrated device.

Indeed, as device/feature dimensions shrink and sensitivity to process details becomes increasingly crucial, strong deviations develop between the characteristics of isolated features and similar features fabricated in a periodic design. Consequently, the ability to characterize an isolated feature, which provides an accurate representation of the actual device, becomes increasingly important. Considering semiconductor devices, many features in such devices are isolated or aperiodic (there is no periodicity of its appearance on a structure, or at least within an illuminated spot), e.g. single line, trench, hole or via, or a specific alignment mark. Such a structure can have extremely small dimensions.

In this connection, it should be understood that for the purpose of the present application, a feature to be measured is such an isolated feature that has a sub-wavelength dimension with respect to a wavelength range used in optical measurements.

Leading optical metrology solutions available today, such as spectral reflectometry and spectral ellipsometry, employ a measurement spot of a few tens of microns in diameter. As stated, these measurement spots cover many identical elements (pattern features/devices), leading to strong reflected signals, and moreover, the measured region is entirely (or at least to a decisive degree) contained inside a test site, so that the measured reflectivity carries information on the measured target, with no (or very minor) effect of the surrounding neighborhood.

Applying optical metrology to nanometer-scale isolated structures poses two main challenges associated with the signal strength and effect of background. More specifically, with regard to the signal strength, it should be understood that reflected signal from a nanometric isolated feature is significantly weaker than that from a periodic array. As for the effect of background, in optical measurement of an isolated feature, contrary to that of large periodic arrays, the majority of the illumination spot will cover regions surrounding the feature to be measured (target feature). Reflections from the adjacent regions will add up into the measurement, and potentially overwhelm the weak reflection from the feature of interest.

The present invention provides a novel metrology technique that allows extremely efficient focusing of an illumination/measurement spot (contrary to reflectometry and ellipsometry) and enables detection of strong signal from the feature being measured, as well as eliminates or at least significantly reduces contribution arising from the optical response of surroundings, highlighting and isolating reflections from the feature of interest, thus ensuring sufficiently high SNR.

The present invention provides a novel method and system for use in measurement of isolated features of a structure. According to the invention, Back Focal Plane Microscopy (BFM) measurements are applied to a structure utilizing dark-field detection mode while applying pinhole masking to incident light propagating through an illumination channel towards the structure. Measured data (detected signal) is thereby indicative of a scattering matrix characterizing scattering properties of the structure, enabling identification of one or more isolated features of the structure. To this end, the scattering matrix can be analyzed using theoretical data (modeled and/or calibrated) to determine the parameters (e.g. critical dimensions, profile) of the isolated feature corresponding to the best fit between the measured and theoretical data.

Thus, according to one broad aspect of the invention, there is provided an optical method for use in measurement of isolated features of a structure, the method comprising:

applying Back Focal Plane Microscopy (BFM) measurements to a structure and obtaining measured data indicative thereof, said BFM measurements comprising performing dark-field detection mode while applying pinhole masking to incident light propagating through the illumination channel towards the structure; and processing the measured data and obtaining data characterizing scattering of said incident light from an illuminated spot on the structure, thereby enabling identification of an isolated feature of the structure.

The pinhole masking procedure includes scanning a Fourier plane of the structure plane by a pinhole and successively collecting light components returned from the structure, and generating the measured data indicative of at least amplitude of a scattering matrix, $S(k_{in},k_{out})$, characterizing the structure, where $k_{in}$ and $k_{out}$ are incident and returned ray vectors respectively. The measured data, corresponding to a detected signal from the structure is proportional to amplitude of the scattering matrix, $|S(k'_{in},k_{out})|^2$.

Preferably, the pinhole masking procedure utilizing said scanning of the Fourier plane by the pinhole by moving said pinhole with respect to an additional static pinhole located in the Fourier plane, and generating the measured data indicative of the amplitude and a phase of the scattering matrix characterizing the structure. Such measured data corresponds to a sum $|S(k_1, k_{out})+S(k_2, k_{out})|^2$ of scattering matrices $S(k_1, k_{out})$ and $S(k_2, k_{out})$ corresponding to measurements through the static and the movable pinholes respectively, $k_{1,2}$ being two incident ray vectors. The determined amplitude can be utilized to extract the phase between the two matrices $S(k_1, k_{out})$ and $S(k_2, k_{out})$.

The dark-field detection mode may further include affecting/modulating polarization of light passing along the illumination and detection channels. This may be implemented by passing the incident light and collected returned light through respectively first and second polarizers accommodated in the illumination and detection channels and having substantially perpendicular planes of polarization. In another example, this can be implemented by passing the incident light and collected returned light through respectively first and second polarizers accommodated in the illumination and detection channels and having substantially parallel planes of polarization, and passing the incident polarized light propagating towards the structure through a phase retarder, and passing the returned light propagating from the structure to the second polarizer through said phase retarder. In yet further example, the incident light and collected returned light pass through a common polarizer and a common phase retarder accommodated in a spaced-apart relationship in a common portion of the illumination and detection channels, with the polarizer being located upstream of the phase retarder with respect to a direction of propagation of the incident light to the structure along the illumination channel.

According to another broad aspect of the invention, there is provided a system for use in measuring features of a structure. The system comprises: a light source unit; a light directing/collecting assembly comprising an objective lens unit and a beams splitter accommodated to define an illumination channel and a detection channel for incident and returned light propagation to and from a structure plane; and a detection unit comprising a light sensitive surface located in a plane conjugate to a back focal plane of the objective lens unit. The light directing/collecting assembly is configured for dark-field detection mode reducing amount of light specularly reflected from the structure in light detected by the light sensitive surface of the detection unit. The light directing/collecting assembly comprises a pinhole mask located in the illumination channel in a back focal plane of the objective lens unit, said pinhole mask comprising a pinhole movable within said back focal plane to thereby scan the structure with light components of different angles of incidence. The detected light is therefore indicative of a scattering matrix characterizing scattering properties of the structure, enabling identification of one or more isolated features of the structure.

The light directing/collecting assembly preferably further comprises a polarization modulating arrangement for affecting polarization of light passing along the illumination and detection channels to thereby implement the dark-field detection mode. Such a polarization modulating arrangement may be configured as described above.

The system is associated with a control unit connectable to the detection unit for receiving and processing measured data indicative of the detected light. The control unit comprises a processor preprogrammed for processing the measured data and determine at least an amplitude of the scattering matrix, $S(k_{in},k_{out})$, characterizing the structure, where $k_{in}$ and $k_{out}$ are incident and returned ray vectors respectively, being indicative of location of the one or more isolated features of the structure.

The pinhole mask preferably comprises the movable pinhole and an additional fixed pinhole. In this case, the detected signals obtained during the movement of the movable pinhole with respect to the static pinhole located in the back focal plane of the objective unit is indicative of the amplitude and a phase of the scattering matrix characterizing the structure. The processor is thus configured for identifying, in the data indicative of the detected light, a sum $|S(k_1, k_{out})+S(k_2, k_{out})|^2$ of scattering matrices $S(k_1, k_{out})$ and $S(k_2, k_{out})$ corresponding to measurements through the static and the movable pinholes respectively, $k_{1,2}$ being two incident ray vectors, and utilizing the determined amplitude and extracting the phase between the two matrices $S(k_1, k_{out})$ and $S(k_2, k_{out})$.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

The present invention provides a novel system for use in optical measuring/inspecting of isolated features in a structure. The system utilizes the principles of Back Focal Plane Microscopy (BFM), which is a variation of imaging microscopy, where image plane (detection plane) is located not in a plane conjugate to the object plane (structure plane) but rather in a plane conjugate to the back focal plane of an objective lens.

Figure 1:
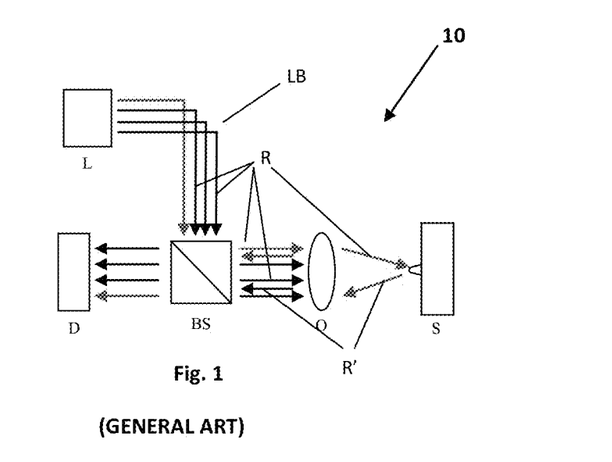
FIG. 1 schematically illustrates the configuration and light propagation scheme in a typical Back Focal Plane Microscope (BFM) setup.

In this connection, reference is made to FIG. 1, showing schematically the configuration of a typical BFM set up and a light propagation scheme therein. The BFM setup 10 includes a light source L, a beam splitter BS, an objective O, and a position sensitive detector D. A light beam LB from the source L is directed onto a sample S under measurements by the beam splitter BS and the objective lens O. Every light component (ray) R of the light beam LB is incident on the sample S at a certain angle and returned (reflected and/or scattered) from the sample. A part of the returned rays R' is collected by the objective O, passes the beam splitter BS and reaches the position sensitive detector D where the rays are recorded. The light sensitive surface of the detector (image plane) is positioned such that rays returned with different angles reach different positions respectively on the detector. In this scheme, the angular dependence of the sample reflectance is measured. The BFM technique can utilize a large Numerical Aperture (NA) objective allowing for a small illumination spot.

Figure 2:
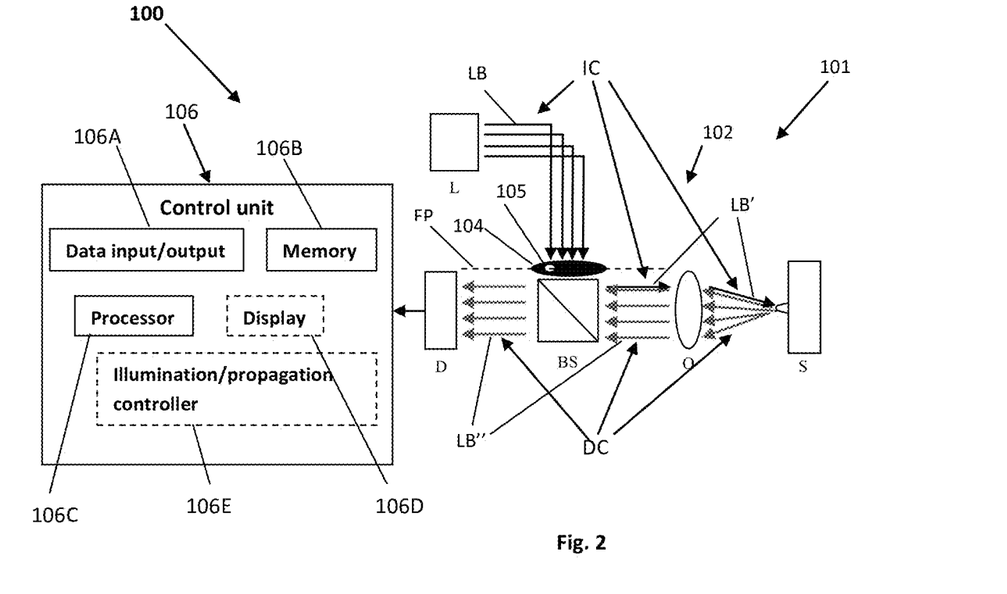
FIG. 2 schematically illustrates the configuration and light propagation scheme in a BFM based optical system of the invention.

Reference is made to FIG. 2 illustrating schematically the configuration of a measurement system according to the invention, and a light propagation scheme in the system. The system 100 of the invention includes an optical system 101 and a control unit 106 configured for communication between them (via wires or wireless signal transmission). The optical system 101 is configured generally similar to the typical BFM, and therefore to facilitate illustration and understanding the same reference marks are used for identifying components that are common in the BFM 10 of FIG. 1 and the system 100 of the invention.

The optical system 101 of the invention is configured as a so-called masked BFM. The system 101 includes a light source unit L (including light emitter(s) and/or light guiding assembly), a detection unit D (including a light sensitive surface possibly associated with imaging optics), and a light directing/collecting assembly 102 including a beam splitter BS and an objective lens unit O (one or more lenses). In the system 100 of the invention, the light directing/collecting assembly 102 additionally includes a pinhole mask 104, which may be a single-pinhole or double-pinhole mask, as will be described further below. The optical system 101 defines an illumination channel IC and a detection channel DC. The pinhole mask 104 is located in the illumination channel IC, being positioned in the back focal plane of the objective lens unit O.

As shown, an illuminating light beam LB propagates along the illumination channel IC and is directed to the beam splitter BS through the pinhole mask 104, being configured as a single-pinhole 105 mask in the present not limiting example, which effects partial masking and thus allows only a small portion LB' (selected angular component) of the light beam LB to reach the beam splitter BS, which directs (reflects in this specific not limiting example) this portion LB' to the objective lens unit 0 that focuses this light LB' onto an illumination spot on a sample S. Light beam LB" returned (reflected and/or scattered) from the illuminated spot propagates along the detection channel DC and is collected by the objective lens unit O and then directed (transmitted) by the beam splitter BS towards the light sensitive surface of the detection unit D. The system 100 operates to move/scan the pinhole 105 position on the mask, i.e. in the back focal plane of the objective being a Fourier plane FP, to thereby vary the angle of incidence. Thus, for each angular component of the incident light multiple angles of propagation of the returned light are directed to the position sensitive detector.

The output of the detection unit D is connectable (via wires or wireless signal transmission) to the control unit 106. The control unit 106 includes a computer system comprising inter alia such functional utilities as data input and output utilities 106A, memory 106B, data processor 106C, and possibly also a display 106D. The control unit 106 may also include a controller 106E for controlling illumination parameters/conditions and/or light propagation parameters/conditions, for example for controlling polarization conditions, as will be described further below.

According to the invention, the above-described system 100 using a pinhole mask 104 configured and accommodated as described above, utilizes a scattering matrix characterization for measuring isolated features on the sample. The scattering matrix, $S(k_{in},k_{out})$, is a function of $k_{in}$ and $k_{out}$ which are the incident and returned ray vectors respectively. Generally, matrix S is a complex function, and by measuring its amplitude and phase the sample's interaction with light can be completely characterized.

The principles of scattering matrix characterization can be used with a BFM-based system of the invention in which a pinhole mask is inserted in the objective's back focal plane in the incident light path, since in such system light is incident on the sample by controlled angles and is eventually detected in angular space. With this configuration, only a specific portion $k'_{in}$ of incident light (LB' in FIG. 2) is allowed to pass and illuminate the sample. The detected signal obtained in such BFM-based system 100 is proportional to $|S(k'_{in},k_{out})|^2$ for each respective position on the detector defined by the value of $k_{out}$. As described above, the pinhole 105 position on the mask can be scanned in a Fourier plane FP (back focal plane of the objective) to thereby vary the angle of incidence and thus obtain a two dimensional characterization of $S(k_{in},k_{out})$ with respect to its two parameters.

The use of a single-pinhole mask (with movable pinhole) allows direct measurement of the scattering matrix amplitude, but it does not provide enough information on the matrix' phase. In order to allow direct determination of the phase of the scattering matrix, a pinhole mask with two holes (pinholes) may be used being located in the back focal plane of the objective. Although this is not specifically illustrated, it should be understood that in this configuration, one of the holes is static (at a fixed location) and the other is movable (scanned) in the Fourier plane (the objective's back focal plane). The signal on the detector is proportional to the sum of the scattering matrices $|S(k_1, k_{out})+S(k_2, k_{out})|^2$, where $k_{1,2}$ are the two incident ray vectors propagated through the static and movable pinholes. As the amplitudes of the scattering matrix were already obtained with the previous technique, this measurement allows to extract the phase between the two components $S(k_1, k_{out})$ and $S(k_2, k_{out})$.

Thus, the control unit 106 (processor) receives data indicative of the detected signals during the scan of the position of the second pinhole, the processor 106C is pre-programmed for processing and analyzing this data and determining the phase difference between the detected signals obtained with the first and second pinholes, and generates output data indicative of the complete characterization of the scattering matrix. Then, the processor may operate to utilize theoretical data (modeled and/or calibrated) data to compare the measured data with the theoretical data and determine the parameters (e.g. critical dimensions, profile) of the isolated feature corresponding to the best fit between the measured and theoretical data.

Generally, alternatively or additionally, the phase of the scattering matrix can be obtained by scanning the sample's position along the optical axis around the focal plane, i.e. a so-called "focus scan" technique. An unmasked BFM scheme relates each detector position to the entire space of incident vectors such that the obtained signal is proportional to $|\Sigma_{k_{in}} S(k_{in},k_{out})|^2$. In the case where the sample is not positioned in the focal point (z=0), the signal on the detector is changed to $|\Sigma_{k_{in}} S(k_{in},k_{out})|^2 \exp(i(k_{in}-k_{out})^2 z)|^2$. A scan of the z position (along the optical axis, or illumination channel axis) provides a complete characterization of the scattering phases.

In order to effectively identify/measure isolated features, dark field mode can be used, e.g. based on polarization effect, in addition to the pinhole mask (single- or preferably double-pinhole mask). The dark-field technique is based on the fact that light specularly reflected from a structure maintains its original polarization (i.e. that of the incident light). As a result, it is possible to differentiate between light components specularly reflected from the wafer top surface (which serves as unwanted background), and light components returned (scattered) from the target feature (e.g. groove). In general, isolated features (and specifically sub-wavelength scatterers) are expected to cause significant polarization rotation, leading to strong contribution to the collected signal.

The examples of implementation of dark-field measurements relying on the polarization effect useful for the technique of the present invention are disclosed in WO 13/011508 and WO 12/098550, both being assigned to the assignee of the present application and being incorporated herein by reference. According to some techniques described in these patent applications, the measurements utilize cross-polarizers in illumination and detection channels, or a common phase-retarder in the illumination and detection channels. According to some other techniques of these patent applications, partial masking (blocking) of both the illumination and detection channels are used (e.g., a masking element in the common/overlapping part of the illumination and detection channels, or complementary masks in the illumination and collection paths), such as to effectively prevent any ray specularly reflected from the top surface of a structure under measurements to be collected by a detector.

Figure 3:
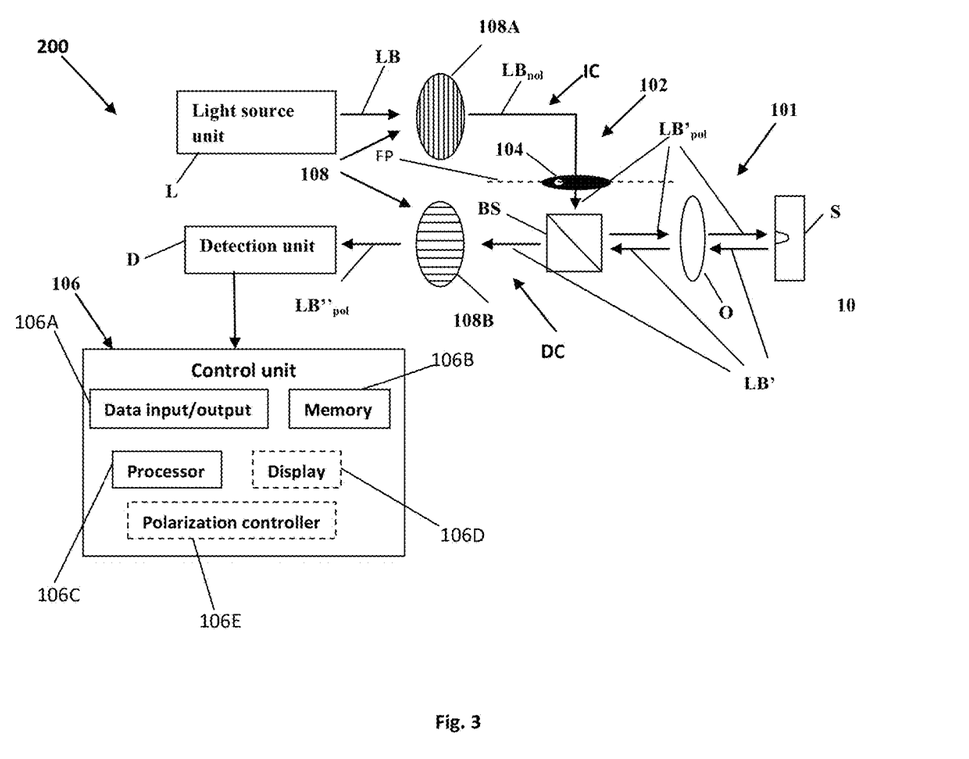
FIG. 3 schematically illustrates the configuration and light propagation scheme in a system of the invention utilizing a combination of polarization-based dark-field mode and scattering matrix characterization technique.

The present invention utilizes the principles of the polarization-based dark-filed technique in a BFM-based system using a pinhole mask. In this connection, reference is made to FIG. 3 schematically illustrating a measurement system 200 of the invention, which is configured generally similar to the above-described BFM-based system 100, in which the light directing/collecting assembly 102 additionally includes a polarization modulating arrangement 108. More specifically, the system 200 includes a light source unit L (which may be constituted by a light emitting arrangement or by a light guiding unit associated with an external light emitter), a detection unit D, and a light directing assembly 102. The light directing assembly 102 includes a beam splitter BS and focusing optics (objective) O accommodated in a common part of the illumination and detection channels IC and DC, and a polarization modulation arrangement 108. The latter is configured to provide mutually perpendicular polarizations for the incident and returned light beams forming a so-called cross-polarized reflectometer. The polarization modulating arrangement 108 includes polarizers 108A and 108B having fixed or controllably tunable planes of polarizations to provide a condition that they are substantially perpendicular to one another. If the tunable polarizer(s) is/are used, the control unit is equipped with an appropriate polarization controller (shown in the figure as a "light propagation controller").

Thus, light beam LB coming from the light source unit L propagates along the illumination channel IC, is polarized by the incident-path polarizer 108A, and resulting polarized light $LB_{poi}$ is incident onto a pinhole mask 104 (having a single- or double-pinhole configuration), which allows propagation of a portion thereof $LB_{poi}$ towards the sample through the beam splitter BS and objective O. Light LB' returned from the illuminated region on the sample S propagates along the detection channel DC being focused by optics O onto the beam splitter BS and directed (transmitted) thereby to the polarizer 108B. This light LB' includes light components specularly reflected from surfaces (within the illuminated spot) and thus having substantially the same polarization as light $LB_{pol}$ and also light components scattered from the sample surfaces (in the illuminated spot), such as the light components returned from the isolated feature, which light components have polarization different from that of light $LB_{pol}$. This returned light LB' interacts with the polarizer 108B, and output polarized light $LB''_{pol}$ propagates to the detection unit D. In light $LB''_{pol}$ emerging from the polarizer 108B, reflected contribution from surfaces within the illuminated spot being perpendicular to the incident light direction is ideally completely suppressed. However, scattered light components which are mainly associated with the isolated feature on the structure, can undergo significant polarization change, allowing at least part thereof to be collected by the detector D.

It should be noted, although not specifically illustrated, that the above-described crossed-polarizer dark field setup may be replaced by a different configuration of the polarization modulating arrangement. For example, it may utilize first and second polarizers have substantially parallel planes of preferred polarization and located in respectively illumination and detection channels, and a phase retarder 17. The latter is located in the common (overlapping) part of the channels (e.g. between the objective and beam splitter) and applies 45° polarization rotation to light passing therethrough. According to yet another possible configuration of the polarization modulation arrangement, it may include a single polarizer and a phase retarder, both located in the overlapping part of the illumination and detection channels, the polarizer being located between the beam splitter BS and the phase retarder.

The system of the present invention may utilize any of the above described polarization-based The dark-field techniques in combination with the scattering matrix retrieval techniques described above, e.g. based on BFM with pinhole masking, to obtain information on the isolated feature, and allow for sub-wavelength dimensional analysis. It should be noted that the system of the invention may utilize a standard bright-field BFM setup, modified to implement polarization-based dark-field and pinhole masking. Also, the invention may utilize sequential implementation of the dark-field and pinhole-masking measurements by any two or more of the above-described techniques, in order to obtain several sets of independent information.

Measured data indicative of the output of the detection unit is processed as described above to provide sample characterization data. In order to deduce information regarding the physical dimensions of the feature being measured, a comparison can be made between the measured BFM data and corresponding theoretical (modeled/calibrated) BFM data for features with similar geometry but varying dimensional and/or material properties parameters of the model. The profile of the measured feature can be thereafter deduced using, for example, a comparison to a large set of calculated BFM images, each of which refers to features of different dimensional properties. Feature dimensions can be extracted by identifying the best-fit calculated image. Alternatively, it is possible to interpolate between calculated BFM images, in order to accurately deduce the dimensional parameters which would yield a best-fit to the measurement.

Thus, the present invention provides a novel simple technique enabling effective detection/identification of isolated features, thereby enabling determination of the feature parameters.

The invention claimed is:

1. An optical method for use in measurement of isolated features of a structure, the method comprising:

performing Back Focal Plane Microscopy (BFM) measurements to the structure and obtaining measured data indicative of scattering properties of the structure with respect to incident light, wherein said BFM measurements are performed using dark-field detection mode, while applying pinhole masking to incident light propagating through the illumination channel towards the structure, wherein said dark-filed detection mode comprises affecting polarization of light passing along the illumination and detection channels by passing the incident light and collected returned light through respectively first and second polarizers accommodated in the illumination and detection channels and having substantially parallel planes of polarization, and passing the incident polarized light propagating towards the structure through a phase retarder, and passing the returned light propagating from the structure to the second polarizer through said phase retarder, such that the measured data corresponding to detected signals from the structure is indicative of a scattering matrix characterizing scattering properties of the structure with respect to the incident light; and processing the measured data using a data processor, said processing comprising applying a fitting procedure between the measured and theoretical modeled data, and identifying an isolated feature of the structure from a best fit condition between the measured and theoretical data.

2. The method according to claim 1, wherein said applying of the pinhole masking to the incident light propagating through the illumination channel comprising scanning a Fourier plane of the structure plane by a pinhole and successively collecting light components returned from the structure, and generating the measured data being indicative of at least amplitude of a scattering matrix, $S(k_{in},k_{out})$, characterizing the structure, where $k_{in}$ and $k_{out}$ are incident and returned ray vectors respectively.

3. The method according to claim 2, wherein the measured data, corresponding to a detected signal from the structure, is proportional to amplitude of the scattering matrix, $|S(k'_{in},k_{out})|^2$.

4. The method according to claim 3, wherein said scanning of the Fourier plane by the pinhole comprises moving said pinhole with respect to an additional static pinhole located in the Fourier plane, and generating the measured data being indicative of the amplitude and a phase of the scattering matrix characterizing the structure.

5. The method according to claim 4, wherein said measured data corresponds to a sum $|S(k_1,k_{out})+S(k_2,k_{out})|^2$ of scattering matrices $S(k_1,k_{out})$ and $S(k_2,k_{out})$ and corresponding to measurements through the static and the movable pinholes respectively, $k_{1,2}$ being two incident ray vectors, the processing of the measured data comprising utilizing the determined amplitude and extracting the phase between the two matrices $S(k_1,k_{out})$ and $S(k_2,k_{out})$.

6. An optical method for use in measurement of isolated features of a structure, the method comprising:

performing Back Focal Plane Microscopy (BFM) measurements on the structure and obtaining measured data indicative of scattering properties of the structure with respect to incident light, wherein said BFM measurements are performed using dark-field detection mode, while applying pinhole masking to incident light propagating through an illumination channel towards the structure, wherein said applying of the pinhole masking comprising scanning a Fourier plane of the structure plane by moving a pinhole defined in a pinhole mask with respect to an additional static pinhole located in the Fourier plane and successively collecting light components returned from the structure, and generating the measured data being indicative of amplitude and phase of a scattering matrix, $S(k_{in},k_{out})$, characterizing the structure, where $k_{in}$ and $k_{out}$ are incident and returned ray vectors respectively, wherein said measured data corresponds to a sum $|S(k_1,k_{out})+S(k_2,k_{out})|^2$ of scattering matrices $S(k_1,k_{out})$ and $S(k_2,K_{out})$ corresponding to measurements through the static and the movable pinholes respectively, $k_{1,2}$ being two incident ray vectors; and processing the measured data using a data processor, said processing comprising utilizing the determined amplitude $|S(k'_{in},k_{out})|^2$ of the scattering matrix as being proportional to the detected light and extracting the phase between the two matrices $S(k_1,k_{out})$ and $S(k_2,k_{out})$, and in accordance with the extracted phase, identifying an isolated feature of the structure.

7. The method according to claim 6, wherein said applying of the dark-field detection mode comprises affecting polarization of light passing along the illumination and detection channels.

8. The method according to claim 7, wherein said affecting of the polarization of light passing along the illumination and detection channels comprises passing the incident light and collected returned light through respectively first and second polarizers accommodated in the illumination and detection channels and having substantially perpendicular planes of polarization.

9. The method according to claim 7, wherein said affecting of the polarization of light passing along the illumination and detection channels comprises passing the incident light and collected returned light through respectively first and second polarizers accommodated in the illumination and detection channels and having substantially parallel planes of polarization, and passing the incident polarized light propagating towards the structure through a phase retarder, and passing the returned light propagating from the structure to the second polarizer through said phase retarder.

10. The method according to claim 7, wherein said affecting of the polarization of light passing along illumination and detection channels comprises passing the incident light and collected returned light through a common polarizer and a common phase retarder accommodated in a spaced-apart relationship in a common portion of the illumination and detection channels, with the polarizer being located upstream of the phase retarder with respect to a direction of propagation of the incident light to the structure along the illumination channel.

11. An optical method for use in measurement of isolated features of a structure, the method comprising:

performing Back Focal Plane Microscopy (BFM) measurements on the structure and obtaining measured data indicative of scattering properties of the structure with respect to incident light, wherein said BFM measurements are performed using dark-field detection mode, while applying pinhole masking to incident light propagating through the illumination channel towards the structure, wherein said dark-filed detection mode comprises affecting polarization of light passing along the illumination and detection channels by passing the incident light and collected returned light through a common polarizer and a common phase retarder accommodated in a spaced-apart relationship in a common portion of the illumination and detection channels, with the polarizer being located upstream of the phase retarder with respect to a direction of propagation of the incident light to the structure along the illumination channel; and processing the measured data using a data processor, said processing comprising applying a fitting procedure between the measured and theoretical modeled data, and identifying an isolated feature of the structure from a best fit condition between the measured and theoretical data.

12. The method according to claim 11, wherein said applying of the pinhole masking to the incident light propagating through the illumination channel comprising scanning a Fourier plane of the structure plane by a pinhole and successively collecting light components returned from the structure, and generating the measured data being indicative of at least amplitude of a scattering matrix, $S(k_{in},k_{out})$, characterizing the structure, where $k_{in}$ and $k_{out}$ are incident and returned ray vectors respectively.

13. The method according to claim 12, wherein the measured data, corresponding to a detected signal from the structure, is proportional to amplitude of the scattering matrix, $|S(k'_{in},k_{out})|^2$.

14. The method according to claim 13, wherein said scanning of the Fourier plane by the pinhole comprises moving said pinhole with respect to an additional static pinhole located in the Fourier plane, and generating the measured data being indicative of the amplitude and a phase of the scattering matrix characterizing the structure.

15. The method according to claim 14, wherein said measured data corresponds to a sum $|S(k_1,k_{out})+S(k_2,k_{out})|^2$ of scattering matrices $S(k_1,k_{out})$ and $S(k_2,k_{out})$ corresponding to measurements through the static and the movable pinholes respectively, $k_{1,2}$ being two incident ray vectors, the processing of the measured data comprising utilizing the determined amplitude and extracting the phase between the two matrices $S(k_1,k_{out})$ and $S(k_2,k_{out})$.

16. A system for use in measuring features of a structure, the system comprising: a light source unit; a light directing/collecting assembly comprising an objective lens unit and a beams splitter accommodated to define an illumination channel and a detection channel for incident and returned light propagation to and from a structure plane; and a detection unit comprising a light sensitive surface located in a plane conjugate to a back focal plane of the objective lens unit; wherein the light directing/collecting assembly is configured for dark-field detection mode reducing amount of light specularly reflected from the structure in light detected by the light sensitive surface of the detection unit, the light directing/ collecting assembly comprising:

a polarization modulating arrangement for affecting polarization of light passing along the illumination and detection channels to thereby implement the dark-field detection mode, said polarization modulating arrangement comprises first and second polarizers accommodated in the illumination and detection channels and having substantially parallel planes of polarization, and a phase retarder accommodated in the illumination and detection channels so as to be in an optical path of the incident polarized light propagating towards the structure plane and in an optical path of the returned light propagating from the structure plane to the second polarizer, and a pinhole mask located in the illumination channel in a back focal plane of the objective lens unit, said pinhole mask comprising a pinhole movable within said back focal plane to thereby scan the structure with light components of different angles of incidence, the detected light being therefore indicative of a scattering matrix characterizing scattering properties of the structure, enabling identification of one or more isolated features of the structure.

17. The system according to claim 16, comprising a control unit connectable to the detection unit for receiving measured data indicative of the detected light, the control unit comprising a processor preprogrammed for processing the measured data and determine at least amplitude of the scattering matrix, $S(k_{in},k_{out})$, characterizing the structure, where $k_{in}$ and $k_{out}$ are incident and returned ray vectors respectively, being indicative of location of the one or more isolated features of the structure.

18. The system according to claim 17, wherein the processor is configured for determining the amplitude of the scattering matrix, $|S(k'_{in},K_{out})|^2$ as being proportional to the detected light.

19. The system according to claim 18, wherein said pinhole mask comprises said movable pinhole and an additional fixed pinhole, the detected signals obtained during the movement of said movable pinhole with respect to the static pinhole located in the back focal plane of the objective unit being indicative of the amplitude and a phase of the scattering matrix characterizing the structure.

20. The system according to claim 19, wherein said processor is configured for identifying, in the data indicative of the detected light, a sum $|S(k_1,k_{out})+S(k_2,k_{out})|^2$ of scattering matrices $S(k_1,k_{out})$ and $S(k_2,k_{out})$ corresponding to measurements through the static and the movable pinholes respectively, $k_{1,2}$ being two incident ray vectors, and utilizing the determined amplitude and extracting the phase between the two matrices $S(k_1,k_{out})$ and $S(k_2,k_{out})$.

21. A system for use in measuring features of a structure, the system comprising: a light source unit; a light directing/collecting assembly comprising an objective lens unit and a beams splitter accommodated to define an illumination channel and a detection channel for incident and returned light propagation to and from a structure plane; a detection unit comprising a light sensitive surface located in a plane conjugate to a back focal plane of the objective lens unit; and a control unit connectable to the detection unit for receiving measured data indicative of the detected light; wherein the light directing/collecting assembly is configured for dark-field detection mode reducing amount of light specularly reflected from the structure in light detected by the light sensitive surface of the detection unit, the light directing/ collecting assembly comprising a pinhole mask located in the illumination channel in a back focal plane of the objective lens unit, said pinhole mask comprising a movable pinhole and an additional fixed pinhole within said back focal plane to thereby scan the structure with light components of different angles of incidence, the detected light signals obtained during the movement of said movable pinhole with respect to the static pinhole being indicative of amplitude and phase of scattering matrix characterizing scattering properties of the structure;

the control unit comprises a processor preprogrammed to process the measured data and determine the amplitude and phase of the scattering matrix, $S(k_{in},k_{out})$, where $k_{in}$ and $k_{out}$ are incident and returned ray vectors respectively, being indicative of location of the one or more isolated features of the structure, the amplitude of the scattering matrix $|S(k'_{in},k_{out})|^2$ being determined as being proportional to the detected light, said processor being configured to identify, in the data indicative of the detected light, a sum $|S(k_1,k_{out})+S(k_2,k_{out})|^2$ of scattering matrices $S(k_1,k_{out})S(k_1,k_{out})$ and $S(k_2,k_{out})S(k_2,k_{out})$ corresponding to measurements through the static and the movable pinholes respectively, $k_{1,2}$ being two incident ray vectors, and utilize the determined amplitude to extract the phase between the two matrices $S(k_1,k_{out})$ and $S(k_2,k_{out})$, and identify an isolated feature of the structure.

22. The system according to claim 21, wherein the light directing/collecting assembly comprises a polarization modulating arrangement for affecting polarization of light passing along the illumination and detection channels to thereby implement the dark-field detection mode.

23. The system according to claim 22, wherein said polarization modulating arrangement comprises first and second polarizers accommodated in the illumination and detection channels and having substantially perpendicular planes of polarization.

24. The system according to claim 22, wherein said polarization modulating arrangement comprises first and second polarizers accommodated in the illumination and detection channels and having substantially parallel planes of polarization, and a phase retarder accommodated in the illumination and detection channels so as to be in an optical path of the incident polarized light propagating towards the structure plane and in an optical path of the returned light propagating from the structure plane to the second polarizer.

25. A system for use in measuring features of a structure, the system comprising: a light source unit; a light directing/collecting assembly comprising an objective lens unit and a beams splitter accommodated to define an illumination channel and a detection channel for incident and returned light propagation to and from a structure plane; and a detection unit comprising a light sensitive surface located in a plane conjugate to a back focal plane of the objective lens unit; wherein the light directing/collecting assembly is configured for dark-field detection mode reducing amount of light specularly reflected from the structure in light detected by the light sensitive surface of the detection unit, the light directing/ collecting assembly comprising:

a polarization modulating arrangement for affecting polarization of light passing along the illumination and detection channels to thereby implement the dark-field detection mode, said polarization modulating arrangement comprising a common polarizer and a common phase retarder accommodated in a spaced-apart relationship in a common portion of the illumination and detection channels, with the polarizer being located upstream of the phase retarder with respect to a direction of propagation of the incident light to the structure plane along the illumination channel, and a pinhole mask located in the illumination channel in a back focal plane of the objective lens unit, said pinhole mask comprising a pinhole movable within said back focal plane to thereby scan the structure with light components of different angles of incidence, the detected light being therefore indicative of a scattering matrix characterizing scattering properties of the structure, enabling identification of one or more isolated features of the structure.

26. The system according to claim 25, comprising a control unit connectable to the detection unit for receiving measured data indicative of the detected light, the control unit comprising a processor preprogrammed for processing the measured data and determine at least amplitude of the scattering matrix, $S(k_{in},k_{out})$, characterizing the structure, where $k_{in}$ and $k_{out}$ are incident and returned ray vectors respectively, being indicative of location of the one or more isolated features of the structure.

27. The system according to claim 26, wherein the processor is configured for determining the amplitude of the scattering matrix, $|S(k'_{in},k_{out})|^2$ as being proportional to the detected light.

28. The system according to claim 27, wherein said pinhole mask comprises said movable pinhole and an additional fixed pinhole, the detected signals obtained during the movement of said movable pinhole with respect to the static pinhole located in the back focal plane of the objective unit being indicative of the amplitude and a phase of the scattering matrix characterizing the structure.

29. The system according to claim 28, wherein said processor is configured for identifying, in the data indicative of the detected light, a sum $|S(k_1,k_{out})+S(k_2,k_{out})|^2$ of scattering matrices $S(k_1,k_{out})$ and $S(k_2,k_{out})$ corresponding to measurements through the static and the movable pinholes respectively, $k_{1,2}$ being two incident ray vectors, and utilizing the determined amplitude and extracting the phase between the two matrices $S(k_1,k_{out})$ and $S(k_2,k_{out})$.

* * * * *